United States Patent
Fritz et al.

(10) Patent No.: US 7,897,826 B2
(45) Date of Patent: Mar. 1, 2011

(54) PROCESS AND PLANT FOR OLIGOMERIZATION/POLYMERIZATION OF ETHYLENE AND/OR ALPHAOLEFINS

(75) Inventors: Peter Fritz, Unterhaching (DE); Heinz Bölt, Wolfratshausen (DE); Anton Kirzinger, Munich (DE); Wolfgang Müller, Munich (DE); Florian Winkler, Munich (DE)

(73) Assignees: Saudi Basic Industries Corporation, Riyadh (SA); Linde AG, Munich (DE)

( * ) Notice: Subject to any disclaimer, the term of this patent is extended or adjusted under 35 U.S.C. 154(b) by 0 days.

(21) Appl. No.: 12/309,873

(22) PCT Filed: Jun. 5, 2007

(86) PCT No.: PCT/EP2007/004968

§ 371 (c)(1), (2), (4) Date: Jan. 30, 2009

(87) PCT Pub. No.: WO2008/014841

PCT Pub. Date: Feb. 7, 2008

(65) Prior Publication Data

US 2009/0247714 A1    Oct. 1, 2009

(30) Foreign Application Priority Data

Jul. 31, 2006    (EP) .................................. 06015892

(51) Int. Cl.
*C07C 2/02*    (2006.01)
*C07C 1/00*    (2006.01)
*C08F 2/00*    (2006.01)
*C08F 110/02*    (2006.01)

(52) U.S. Cl. ...................... 585/502; 585/315; 585/330; 585/506; 526/67; 526/352

(58) Field of Classification Search ............. 526/124.1, 526/72, 67, 68; 585/330
See application file for complete search history.

(56) References Cited

U.S. PATENT DOCUMENTS

| 3,280,095 | A | | 10/1966 | Lyon |
| 3,817,969 | A | | 6/1974 | Mueller-Tamm |
| 4,832,920 | A | * | 5/1989 | Owen et al. .................. 422/190 |
| 5,981,818 | A | | 11/1999 | Purvis |
| 6,121,502 | A | * | 9/2000 | Tembe et al. ................. 585/524 |

FOREIGN PATENT DOCUMENTS

| EP | 1001001 A | | 5/2000 |
| EP | 1001001 A1 | * | 5/2000 |
| WO | WO 2006018071 A1 | * | 2/2006 |

* cited by examiner

*Primary Examiner*—David Wu
*Assistant Examiner*—Elizabeth Eng
(74) *Attorney, Agent, or Firm*—Kramer Levin Naftalis & Frankel LLP

(57) ABSTRACT

The present invention relates to a process for oligomerization/polymerization of ethylene and/or alpha-olefins, comprising the steps of oligomerizing/polymerizing ethylene and/or alpha-olefins to produce a reaction product which contains undesired reaction by-products, separating the reaction by-product from the reaction product as one or more reaction by-product fractions, and subjecting at least one of the reaction by-product fractions to steam cracking to produce a steam cracking product which comprises ethylene, which may be optionally purified and feed to the oligomerization/polymerization of ethylene and/or alpha olefins step.

9 Claims, No Drawings

PROCESS AND PLANT FOR OLIGOMERIZATION/POLYMERIZATION OF ETHYLENE AND/OR ALPHAOLEFINS

The present invention relates to a process for oligomerization/polymerization of ethylene and/or alpha-olefins and to a plant therefore.

The oligomerization/polymerization of ethylene and/or alpha-olefins using an organometallic catalyst, suitably in an organic solvent, is widely known in the art. Especially in case of the oligomerization of ethylene a broad product spectrum is obtained reaching from desired $C_4$-$C_{20}$ linear alpha olefins (LAO), to higher linear alpha olefins having more than 20 carbon atoms and to already polymeric products. After oligomerization/polymerization the product has thus to be separated into marketable products and non-marketable fractions comprising offspec products. Non-marketable fractions may comprise products or product fractions which do not fulfill the defined or guaranteed product specifications (i. e. offspec products), or products which are not marketable due to economic reasons. Economic reasons may be given due to the non-availability of adequate infrastructure for processing, handling, or e. g. loading facilities. In addition, marketing of a specific product or fraction may not be economically due to production of only small quantities, high transport and logistics cost and low market price in a certain region.

In the prior art, this non-marketable or offspec fractions or products are usually incinerated, as it is believed that incineration is the most economical route for disposal of non-marketable products.

However, there is a significant negative impact on environmental balance due to incineration and the generation of carbon dioxide.

It is therefore an object of the present invention to provide a process for oligomerization/polymerization of ethylene and/or alpha-olefins which overcomes the drawbacks of the prior art. Especially a process shall be provided which avoids incineration of non-marketable fractions or products, but enables an alternative route for further use thereof.

Additionally, a plant for oligomerization/polymerization shall be provided.

The first object is achieved by a process for oligomerization/polymerization of ethylene and/or alpha-olefins, comprising the steps of oligomerizing/polymerizing ethylene and/or alpha-olefins, separating the product obtained into at least one marketable product and one or more non-marketable fractions and routing one or more of the non-marketable fractions to a steam cracking furnace for steam cracking thereof.

Preferably, ethylene is oligomerized in the first step to form linear alpha olefins.

In one embodiment, prior to separating, a catalyst used for oligomerization/polymerization may be deactivated and/or removed, and solvent utilized in oligomerization/polymerization may be removed.

The separation of marketable and non-marketable oligomerization/polymerization fractions or products may be easily achieved by distillation, filtration or the like.

More preferably, steam cracking products, preferably ethylene, are recycled into the oligomerizing/polymerizing step after adequate separation and purification.

The second object is achieved by a plant for oligomerization/polymerization of ethylene and/or alpha-olefins comprising an oligomerization/polymerization reactor and a steam cracking furnace connected therewith.

Preferably, the steam cracking furnace has a recycling line for recycling steam cracking products to the oligomerization/polymerization reactor downstreams of corresponding separation and purification devices.

Surprisingly, it was found that in the inventive process the non-marketable or offspec fractions or products of the oligomerization/polymerization of ethylene and/or alpha-olefins may be advantageously transferred to a steam cracking furnace to convert these non-marketable streams into steam cracking products having a high ethylene yield. It was further found that the overall economics of the petrochemical complex comprising the inventive plant are substantially improved. Additionally, there is a positive impact on environmental balance by avoidance of incineration.

Steam cracking is widely known in petrochemical industry. Steam cracking is a process in which usually saturated hydrocarbons are broken down into small, often unsaturated, hydrocarbons. It is the principle industrial method for producing lighter alkenes, including ethylene and propene.

In steam cracking, a gaseous or liquid hydrocarbon feed like naphtha, LPG or ethane is diluted with steam and then shortly heated in a furnace (obviously without the presence of oxygen). Typically, the reaction temperature is very high—around 850° C.—but the reaction is only allowed to take place very shortly. The products produced in the steam cracking reaction depend on the composition of the feed, the hydrocarbon to steam ratio and on the cracking temperature and furnace residence time.

So far, there was no suggestion in the prior art to combine a typical oligomerization/reaction reactor with a steam cracking furnace.

According to the process of the present invention monomers, such as ethylene and alpha-olefins, are introduced into an oligomerization/polymerization reactor, preferably in the presence of an organic solvent and a homogenous catalyst. The homogenous catalyst may preferably comprise a zirconium component and an organoaluminum component. The zirconium component may have a formula $ZrCl_{4-m}X_m$, wherein X=OCOR or $OSO_3R'$ and R and R' being independently alkyl, alkene and phenyl, and wherein $0<m<4$. The organoaluminum compound may be preferably $Al(C_2H_5)_3$, $Al_2Cl_3(C_2H_5)_3$ or $AlCl(C_2H_5)_2$. In the oligomerization/polymerization reactor a product is obtained comprising marketable and non-marketable (offspec) fractions or products, which are to be separated. After oligomerization/polymerization the catalyst is deactivated and removed, optionally with removal of the solvent, and the fractions are separated, for example by distillation or filtration if solid high molecular weight oligomers are obtained.

One or more of the non-marketable fractions are then routed to a steam cracking furnace wherein these fractions may be converted into typical steam cracking products, especially ethylene is obtained in high yield. After separation and purification the ethylene may then be recycled into the oligomerization/polymerization reactor or may be utilized for other purposes.

The inventive process avoids the so far utilized incineration of non-marketable fractions or products and adds to the overall economics of the plant.

The features disclosed in the foregoing description and in the claims may, both separately and in any combination thereof, be material for realizing the invention in diverse forms thereof.

The invention claimed is:

1. A process for the oligomerization/polymerization of ethylene and/or alpha-olefins, comprising the steps of oligomerizing/polymerizing ethylene and/or alpha-olefins to produce a reaction product comprising a $C_4$-$C_{20}$ product fraction and reaction by-products having more than 20 carbon atoms, separating the reaction by-products from said product fraction as one or more reaction by-product fractions and subjecting at least one of said reaction by-product fractions to steam cracking to produce a steam cracking product.

2. The process according to claim 1, wherein ethylene is oligomerized in the first step to form a reaction product comprising linear alpha olefins.

3. The process according to claim 2, wherein a catalyst is used in the oligomerization/polymerization step and the catalyst is deactivated and/or removed from the reaction product.

4. The process according to claim 1, wherein the steam cracking product is fed to the oligomerizing/polymerizing step.

5. The process according to claim 2, wherein an oligomerization is carried out utilizing a homogeneous catalyst comprising a zirconium compound and an organoaluminum compound.

6. The process according to claim 5, wherein the zirconium compound has the formula $ZrCl_{4-m}X_m$, wherein X=OCOR or $OSO_3R'$ with R and R' being independently alkyl, alkene and phenyl, and wherein $0<m<4$.

7. The process according to claim 6, wherein the organoaluminum compound is $Al(C_2H_5)_3$, $Al_2Cl_3(C_2H_5)_3$ or $AlCl(C_2H_5)_2$.

8. The process according to claim 4, wherein the steam cracking product comprises ethylene.

9. The process according to claim 8, wherein the steam cracking product is purified to concentrate the ethylene prior to feeding the steam cracking product to the oligomerizing/polymerizing step.

* * * * *